(12) United States Patent
Grunwald et al.

(10) Patent No.: US 7,396,507 B2
(45) Date of Patent: Jul. 8, 2008

(54) METHOD OF MICROBIAL REDUCTION AND/OR STERILIZATION OF IMPRESSION MATERIALS

(75) Inventors: Martin Grunwald, Pulheim (DE); Birgit Esser, Grevenbroich (DE)

(73) Assignee: Heraus Kulzer GmbH & Co. KG, Hanau (DE)

( * ) Notice: Subject to any disclaimer, the term of this patent is extended or adjusted under 35 U.S.C. 154(b) by 667 days.

(21) Appl. No.: 10/462,486

(22) Filed: Jun. 16, 2003

(65) Prior Publication Data

US 2004/0009093 A1  Jan. 15, 2004

(30) Foreign Application Priority Data

Jun. 25, 2002  (DE) .................. 102 28 420

(51) Int. Cl.
*A61L 2/08* (2006.01)
*A61L 2/00* (2006.01)
*A61C 15/00* (2006.01)

(52) U.S. Cl. ................. 422/26; 422/27; 422/292; 422/295; 422/298; 422/300; 422/305; 422/307; 433/216; 433/229

(58) Field of Classification Search ........ 422/1, 422/26, 292, 295, 298, 300, 305, 307; 433/216, 433/229
See application file for complete search history.

(56) References Cited

U.S. PATENT DOCUMENTS 2,223,629 A * 12/1940 Lange .................... 249/81
3,345,497 A * 10/1967 Porteous ................ 219/417
4,033,774 A * 7/1977 Johnson et al. ............ 106/35
4,273,902 A * 6/1981 Tomioka et al. .......... 525/478
4,995,540 A * 2/1991 Colin et al. ............. 222/132
5,624,636 A * 4/1997 Schwartz ................. 422/37
5,947,278 A * 9/1999 Sawhney et al. ......... 206/216

FOREIGN PATENT DOCUMENTS

| DE | 1 745810 | | 1/1970 |
| DE | DT2702670 A 1 | | 7/1977 |
| DE | 29 08 087 | A1 | 2/1980 |
| DE | 37 24 243 | A1 | 2/1989 |
| DE | 37 32 379 | A1 | 4/1989 |
| DE | 38 38 587 | A1 | 5/1990 |
| DE | 37 41 575 | C2 | 6/1990 |
| DE | 101 04 079 | A1 | 8/2002 |
| EP | 0 164 190 | A2 | 11/1985 |
| EP | 0 173 085 | B1 | 3/1986 |
| EP | 0 269 819 | B1 | 6/1988 |
| JP | 52-13234 | | 4/1977 |
| JP | WO 01/89588 | A1 * | 11/2001 |
| WO | WO 99/15132 | | 4/1999 |
| WO | WO 00/07546 | | 2/2000 |
| WO | WO 01/10335 | A1 * | 2/2001 |
| WO | 01 89588 | A1 | 11/2001 |

OTHER PUBLICATIONS

European Search Report for EP 03012767 dated Aug. 29, 2003.
Patent Abstracts of Japan 07112910 A, Feb. 5, 1995; Yasuo et al.

* cited by examiner

*Primary Examiner*—Jill Warden
*Assistant Examiner*—Monzer R Chorbaji
(74) *Attorney, Agent, or Firm*—Serle I. Mosoff; Norris McLaughlin & Marcus, PA

(57) ABSTRACT

The present invention provides a method of microbial reduction and/or sterilization of impression materials, specifically elastomeric impression materials, by means of steam sterilization.

15 Claims, No Drawings

METHOD OF MICROBIAL REDUCTION AND/OR STERILIZATION OF IMPRESSION MATERIALS

The present invention provides a method of microbial reduction and/or sterilization of impression materials, specifically elastomeric impression materials.

Various kinds of impression compounds are already known (see R. G. Craig, Restorative Dental Materials, The C.V. Moosbe-Comp. St. Louis, Toronto, London, 1980, 1979 pp.). Such materials are subject to very high requirements (compare K. Eichner, *Zahnärztliche Werkstoffe und ihre Verarbeitung*, Vol. 1, A. Publisher: Hüthig Verlag, Heidelberg, 4$^{th}$ Edition, 1981, 45 pp.) including:

1. Compound should have a pleasant aroma and flavor, and pleasing appearance.
2. Compound must not contain any toxic or irritating substances.
3. Compound must maintain long-term storage stability (several months).
4. Compound must allow cost-effective manufacturing and facilitate precise impressions.
5. Compound must be easy to handle.
6. Hardening properties must meet clinical requirements.
7. Cured compound must be elastic without suffering permanent deformation under tension stress.
8. Cured compound must have sufficient compression strength and must not break.
9. At room temperature and normal humidity, cured compound must maintain dimensional stability so that accurate dental plaster impressions can be created within an appropriate period of time.
10. Cured compound must not cause dental plaster damage and must be compatible with other impression compounds.

From the group of various available materials, elastomeric impression materials are particularly beneficial, inter alia due to advantageous application and mechanical properties compared to non-elastomeric impression materials.

Several types of elastomeric impression materials are known, such as polymeric elastomers, which set through an addition reaction (e.g. addition crosslinking silicone impression materials, so-called A-silicones, that react with each other by a hydrosilation reaction of vinyl groups on a polydiorganyl group containing polymer (vinyl polymers) with an SiH group containing polydiorganosiloxane (SiH crosslinking agents), forming elastomeric or polyether materials (e.g. as described in DE-A1-37 41 575 and DE-A1-38 38 587) or impression compound that forms elastomers by way of condensation reactions, such as condensation crosslinking silicone impression materials, so-called C-silicones, or polyether impression materials (e.g. as described in DE 101 04 079.2-42 and e.g. in EP 0 269 819 B1 appreciated therein). Other frequently used elastomeric impression materials are those with polyether chains and aziridine group crosslinking (e.g. as described in DE-B-17 45 810); also known are polyether impression materials with acrylate or methacrylate groups, e.g. from EP 0 173 085). These types of impression material basically meet the above-mentioned general requirements for impression materials. They also offer improved storage and stability to disinfectants, compared to highly aqueous materials (e.g. so-called agar-agar hydrocolloids and alginate impression materials), as well as providing significantly increased mechanical stability.

As a rule, these elastomeric impression materials have a paste-like consistency before setting (i.e. before developing their elastomeric structure). They usually consist of two components (often referred to as a base paste and a catalytic or hardening paste) and set to elastomers after being mixed.

In the above-mentioned medical applications, e.g. to build a replacement part or for diagnostic reasons, a negative replica of a certain aspect of human body geometry is made. This requires a precise impression. Elastomeric impression materials are highly efficient for this purpose, as they demonstrate a high degree of accuracy and excellent dimensional stability in storage. Furthermore, they allow disinfection without significant adverse physical property changes. This is of high importance with regard to controlling microbial contamination on human body parts during subsequent procedures, such as model creation, restoration work etc., and can constitute a hazard to persons that handle the impressions and replacement parts fabricated therewith. This is why there are various methods of disinfection for cured impressions (e.g. with $H_2O_2$, ultraviolet light rays, application of disinfectants (e.g. see F. M. Blair, R. W. Wassell, British Dental Journal, Vol. 180, No. 10, 1996, Page 369 pp., and G. L. Adabo, E. Zanarotti, R. G. Fonseca, C. A. Cruz, Journal of Prosthetic Dentistry 81 (5), 1999, Page 621 pp.) or gamma-ray sterilization of impressions (e.g. in J. Setz, U. Benzing, *Deutsche Zahnärztliche Zeitschrift*, 44, 1989, Page 106 pp.)). However, all of these procedures are applied to 'set up', i.e. elastomeric impressions.

With the above mentioned applications, making an impression frequently results in the pasty impression material coming in contact with injured skin, mucosal or bone tissue (e.g. when mucosal bleeding occurs during dental impressions, impression for insertion of implants, impression over unhealed skin tissue in epithetic treatment, or during skin molding).

When body parts come in contact with impression materials, there is naturally the risk of microbial contamination (such as bacteria, bacilli, fungi, yeasts, and viruses) from the impression materials, the primary packaging, or the application accessories (e.g. mixing cannulae for impression materials, which come in two-chamber cartridges, or mixing spatula). This microbial contamination may result in serious health problems with extremely negative consequences for persons with a compromised immune system.

Thus, there have been numerous attempts to find measures to eliminate this hazard.

In this context, in the Journal of Prosthetic Dentistry, 1972, Pages 419-422, D. N. Firtell, D. J. Moore and G. B. Pelleu Jr. described a method of sterilization of alginate powder with ethylene oxide gassing.

While this method is suitable for powdery materials, it cannot easily be adapted for use with impression pastes. Also, as mentioned above, alginate impression materials demonstrate inferior material and application properties compared to elastomeric impression materials. Furthermore, due to inconvenient handling of the described powder and water mixture, this method has not enjoyed wide dissemination.

The goal then was to develop a low-contamination, or even sterile, impression by adding germicidal additives to impression materials. A substance preventing microbial growth was added to the materials (e.g. DE 37 24 243, JP 07112910, WO 99/15132, WO 00/07546). This solution, however, has the possibility of causing property changes in the impression material. Above all, every additive has the disadvantage of contaminating the relevant body part and causing local irritation or possible intolerance and allergic reactions to the active ingredients. Furthermore, with regard to certain microbes, antimicrobial agents are generally used with limited success. In *ZWR*, Vol. 110, 2001, Page 22-26, Th. Kaus and A. Sethi describe the use of a radiation-sterilized tray and a radiation-sterilized mixing cannula for an impression material in a cartridge system, but not the use of sterilized impression material.

An example of gamma-ray irradiation treatment of plastics suitable for dental applications is available through JP 52013234 B4. However, the materials described therein are not usable as impression compounds.

U.S. Pat. No. 4,033,774 describes a thermoplastic, non-elastomeric dental impression material, which is said to be suitable for autoclave sterilization prior to use. However, no further details are provided. A solution regarding possible microbial reduction for elastomeric impression materials is not described.

It is the purpose of the invention to provide a method of safe microbial reduction for impression materials, specifically for pasty, two-component, elastomeric impression materials, without the addition of any additives to the impression material pastes.

The invention meets said purpose through the features of claim 1. Advantageous details are included in the dependent claims. Surprisingly, it was found that steam sterilization, preferably in an autoclave, resolves the problem, particularly when materially compatible and temperature-stable packaging and accessories are used. With this, microbial reduction of the (pasty), preferably two-component, crosslinked elastomeric impression material, to include primary packaging and application accessories, is achieved in one step.

This is even more astonishing, as preliminary testing revealed that the impression material suffers irreparable damage by sterilization with dry heat (4 hrs, 160° C.), which prevents elastomeric crosslinking.

The principle of steam sterilization (for microbial reduction and/or sterilization) in an autoclave is basically already known and widely applied. A comprehensive procedure description and typical sterilization conditions are described e.g. in Monograph K. H. Wallhäußer, *Praxis der Sterilisation—Desinfektion—Konservierung—Keimidentifizierung—Betriebshygiene*, $3^{rd}$ Edition, Publisher: Georg Thieme, Stuttgart—N.Y., 1984, Pages 169 pp.

Preferably, steam sterilization time should not be less than 15 minutes, at a minimum temperature of 121° C.

Especially advantageous are steam sterilization conditions of 25 minutes of sterilization time at a steam pressure of 2.2 bar and a temperature of 136° C.

The major benefit of steam sterilization in an autoclave lies in the fact that such equipment is widely used, and the relevant sterilization can be self-performed on suitable material provided to medical/dental personnel. Another benefit of the steam sterilization method in an autoclave for microbial reduction is that for reaching the desired goal, no potentially hazardous substances need to be handled or added to the material.

It is particularly advantageous, when the pasty impression material is packaged with sufficient material for one single application. Suitable package means are cans, tubular bags, tubes, syringes, and especially two-chamber cartridges.

Contrary to tubes or cans, two-chamber cartridges allow direct material dispensing and mixing by means of a sterilizable mixer without further manual mixing.

Selecting package and accessory materials requires attention to material that will not suffer damage during steam sterilization conditions.

For steam sterilization of silicone impression materials, two-chamber cartridges (which are already known for this field of application) should preferably contain cartridges made of e.g. polypropylene or polyamide 6. Stoppers should be made of polypropylene with polyamide 66 sealing plugs or sealing washers made of steam-sterilizable rubber. Recommended plungers are two-lip or O-ring plungers made of polyamide 6 with silicone O-rings. In principle, other steam sterilization-stable materials may also be used, provided that they are compatible with the relevant type of impression material.

In a typical design, the two-component pasty impression material inside the primary package together with the accessories required for mixing and application, is heat-sealed in a sterilization package that is one-way steam permeable (representing the state of the art in medical steam sterilization) and is placed into the autoclave for steam sterilization.

In a preferred design, such precision impression material in an adequate steam sterilizable two-chamber cartridge, together with the proper static mixers, is heat-sealed in a transparent sterilization package that is one-way steam permeable, and is placed into the autoclave for steam sterilization. A microbially-reduced kit is directly available for application, with sterile outer packaging that is opened immediately prior to the application, thereby offering material with a reduced microbial population for impression taking.

Steam sterilization may be performed immediately prior to application or earlier, i.e. before distribution to the retail market or user. Steam-sterilized kits that are heat-sealed in a sterilizing package are preferred, since microbial reduction of all individual components that might come in contact with the patient during application, is maintained until the user opens the package.

If steam sterilization in an autoclave is performed immediately prior to application, cool-down times must be observed, in order to prevent possible harmful application of materials significantly exceeding the treated patient's body temperature and to warrant the material properties of the impression materials. The application of impression material at room temperature (18-25° C.) is preferred.

If steam sterilization in an autoclave is performed at an earlier point of time, the interim storage requirements recommended for the specific impression material must be met to ensure relevant material property stability.

Additionally, said microbially reduced material is ideally suited for transfer of biologically or medicinally active structures by micro contact printing. Due to microbial reduction of the prepared printing material, the risk of introducing microbes into the printing substrate or onto the printed surface structures during handling of biologically or medicinally active materials is significantly decreased. Micro contact printing techniques are basically known—essential characteristics are described e.g. in Y. Xia, G. M. Whitesides, *Angew. Chem., Int. Ed.* 1998, 37, Pages 550-575.

In the following, the invention will be exemplified without being narrowed. Unless stated otherwise, microbial reduction has been performed by heat-sealing the impression compounds including their accessories in primary packaging consisting of transparent, one-way steam permeable sterilization packaging (e.g. MELAfol® by the MELAG oHG company), and subsequent steam sterilization in an autoclave (e.g. Type 29 by the MELAG oHG company) for a minimum of 25 minutes at 136° C. and 2.2 bar steam pressure.

EXAMPLE 1

Comparable Example

A commercial dental impression compound on the basis of addition crosslinking silicone (A-silicone) (Flexitime Mono Phase, available in temperature-stable, two-chamber cartridges) is subjected to dry-heat sterilization (4 hours, 160° C.).

Subsequent to cooling down to room temperature, the material was incapable of crosslinking into an elastomeric body.

EXAMPLE 2

Comparable Example

A commercial, pasty, two-component A-silicone impression compound (Provil Novo Medium C.D. 2) is filled into a two-chamber cartridge with plunger and gasket of the closing cap of polyethylene (not steam-sterilizable) and subjected to steam sterilization. Plunger and cap melted, making the material useless. The material properties, however, did not experience any significant changes by the steam sterilization.

EXAMPLE 3

Invention

A commercial dental impression compound on the basis of addition crosslinking silicone (Flexitime Mono Phase in temperature-stable, two-chamber cartridges) is physically and application-specifically examined, a) without pre-treatment and b) subsequent to microbial reduction through steam sterilization.

Physical test results:

|  |  | Untreated | Steam-sterilized |
|---|---|---|---|
| Base viscosity | [Pas] | 197 | 411 |
| Catalyst viscosity | [Pas] | 164 | 298 |
| Working time | [min] | 3.55 | 4.30 |
| Recovery from deformation | [%] | 99.4 | 98.4 |
| Shore A hardness at 10 min |  | 58 | 60 |
| Dimensional change | [%] | 0.19 | 0.16 |

Application-specific testing has not revealed any significant property changes upon steam sterilization.

Subsequent to steam sterilization, the impression compound still fully meets the requirements for dental impressions and the requirements according to EN 24823.

EXAMPLE 4

Invention

An addition crosslinking silicone impression material (Flexitime Mono Phase) and an accessory item (mixing nozzle) have been subjected to a microbiological examination (sterility test) prior and subsequent to steam sterilizing.

|  | Not steam-sterilized | | Steam-sterilized | |
|---|---|---|---|---|
|  | Microbial count bacteria [KBE (UFC) value] | Microbial count fungi, yeasts [KBE (UFC) value] | Microbial count bacteria [KBE (UFC) value] | Microbial count fungi, yeasts [KBE (UFC) value] |
| Mixing nozzle | 30 | 10 | no propagable microorganisms detected | no propagable microorganisms detected |
| A-silicone impression material (Flexitime Mono Phase)* | <10 | <10 | no propagable microorganisms detected | no propagable microorganisms detected |

*In test cultures (validation of sterility test (direct inoculation) (in accordance with EP Suppl. 2001), microorganism growth (*bacillus subtilis*, *Pseudomonas aeruginosa*, *Clostridium sporogenes*, *staphylococcus aureus*, *Candida albicans*, *Aspergillus niger*) occurred to the same degree as in the reference cultures (the method is thereby valid).

EXAMPLE 5

Invention

A pasty, two-component A-silicone impression compound is filled in a polypropylene two-chamber cartridge with non-steam-sterilization-stable caps and plungers and in those with steam-sterilization-stable plungers and in a polyamide two-chamber cartridge with steam-sterilizable plungers and caps. The tested, untreated and steam-sterilized materials were re-examined after one month.

By analogy, a condensation crosslinking, two-component, pasty, polyether impression material was tested prior and subsequent to steam sterilization.

The test data are listed in the table below:

| Material | A-Silicone Impression Material, Flextime Mono Phase 1:1 | | | | Polyether Impression Material with Condensation Crosslink Properties (4:1) | |
|---|---|---|---|---|---|---|
| Packaging | PP cartridge with non-temperature-stable, two-lip plunger and non-temperature-stable cap | Temperature-stable two-chamber cartridge system (PA) with temperature-stable plungers and caps | | PP cartridge with temperature-stable plunger and temperature-stable cap | Temperature-stable (1:1) cartridge system (same components as with Flexitime Mono Phase) | Standard (4:1)-CD-system (non-temperature-stable plungers and cap) |
| Mixed with | Green mixing nozzle, non-sterile | Green mixing nozzle, non-sterile | Green mixing nozzle, steam-sterilized | Green mixing nozzle, steam-sterilized | Manual mixing | (4:1) mixing nozzle |
| Treatment | Without "0 test"/ (at 1 month @ 30° C.) | Untreated (at 1 month @ 30° C.) | Steam-sterilized 25 min/136° C./2.2 bar/ (at 1 month @ 30° C.) | Steam-sterilized (25 min/136° C./ 2.2 bar)/ (at 1 month @ 30° C.) | Steam-sterilized (25 min/136° C./2.2 bar) | Untreated ("0 test") |
| Time of seating in patient's mouth [min] | 2.5 | 2.5 | 2.5 | 2.5 | 3.0 | 3.5 |
| Base viscosity [Pas] | 193/(210) | 223/(217) | 542/(387) | 526/(388) | 193 | 85 |
| Catalyst viscosity [Pas] | 170/(200) | 174/(197) | 387/(308) | 350/(256) | 48 | 90 |
| Working time [min] | 2.50/(2.55) | 2.55/(2.75) | 2.70/(2.80) | 2.60/(2.60) | 1.80 | 1.65 |
| Set-up time [min] | 3.20/(3.40) | 3.40/(3.65) | 3.60/(3.85) | 3.45/(3.55) | 3.55 | 2.75 |
| Recovery from deformation | 98.95/(not defined) | not defined | 98.55/(not defined) | 98.58/(not defined) | — | — |
| Shore A, 10 min | 57/(not defined) | not defined | 58/(not defined) | 59/(not defined) | — | — |
| Shore A, 1 h | 58/(not defined) | not defined | 59/(not defined) | 59/(not defined) | — | — |
| Dimension change [%] | 0.25/(not defined) | not defined | 0.27/(not defined) | 0.30/(not defined) | — | — |

It can be stated that A-silicone impression compounds have not suffered significant changes with regard to recovery from deformation, Shore A-hardness or dimensional stability through steam sterilization. As shown in Example 2, thermal treatment increases the viscosity values (caused by the contained structure agent). However, this process is—at least in part—reversible, as confirmed by the one-month-values. Besides a slight slowdown, no negative effect on crosslinking kinetics has been detected. Inside the package, the material is storage-stable with and without prior steam sterilization, as shown by re-measuring after one month.

Polyether impression material does not demonstrate any significant adverse effects in its physical parameters, either. Subsequent to steam sterilization, A-silicone impression compound and polyether impression compound were still acceptable for application.

EXAMPLE 6

Invention

Subsequent to steam sterilization, a microbial count was performed on a condensation-crosslinking polyether impression compound and a condensation-crosslinking silicone impression compound. In both cases, no propagable microorganisms have been detected.

EXAMPLE 7

Invention

Commercial, two-component polyether material (Impregum Garant L Duo Soft in two-chamber cartridges, 2:1), crosslinking through aziridine groups, was subjected to steam sterilization in a steam-sterilization-stable, two-chamber cartridge and afterwards physically tested and compared to untreated material.

| | | Aziridine polyether impression compound (untreated) | Aziridine polyether impression compound (steam-sterilized) |
|---|---|---|---|
| Base viscosity | [Pas] | 83 | 121 |
| Catalyst viscosity | [Pas] | 148 | 176 |
| Working time (OSC measurement) (30 s after manual mixing) | [min] | 2.50 | 2.00 |
| Set-up time (OSC measurement) (30 s after manual mixing) | [min] | 3.50 | 2.80 |
| Recovery from deformation (30 s after manual mixing) | [%] | 98.6 | 98.6 |

Despite the detected changes in viscosity and crosslinking kinetics, material properties after steam sterilization still meet material and application-specific requirements

The invention claimed is:

1. A method of eliminating microbial contamination of two-component pasty crosslinkable elastomeric impression materials comprising subjecting the materials to one-step simultaneous steam sterilization at a temperature and for a time sufficient to effectively eliminate the microbial contamination.

2. A method according to claim 1, wherein the primary packaging and the accessories remain stable under steam sterilization conditions, and the primary packaging and the accessory material have no impact on the material properties of the impression material and/or its components.

3. A method according to claim 1, wherein the impression material and/or its components are arranged inside the primary packaging and subjected to steam sterilization, together with accessories in sterilizing packaging.

4. A method according to claim 3, wherein a steam-sterilization stable, two-chamber cartridge with steam-sterilization stable plungers and caps is used for packaging, and mixing nozzles for accessories.

5. A method according to claim 1, wherein addition, or condensation-crosslinking silicone impression materials, and/or addition, condensation, or aziridine-group crosslinking polyether impression materials, and/or impression materials with crosslinking acrylate or methacrylate groups are used.

6. A method of obtaining an impression of a body part of a patient in the field of dentistry, orthopedics, epithetics, reconstructive surgery, for modeling purposes in the field of ENT and veterinary medicine, and for modeling of skin parts comprising applying an appropriate amount of a material selected from the group consisting of addition-crosslinking silicone impression materials, condensation-crosslinking silicone impression materials, addition, condensation, and aziridine-group crosslinking polyether impression materials, and impression materials with crosslinking acrylate or methacrylate groups where the material has had microbial contamination eliminated according to the method of claim 1.

7. The method of claim 1 where packaging and application accessories for the impression materials are subjected to steam sterilization concurrently with the impression materials.

8. The method of claim 7 where the impression material, the packaging and accessories are heat sealed in a one-way steam permeable package and the package is steam sterilized in an autoclave.

9. The method of claim 7 where the impression material is an addition crosslinking silicone and the packaging is selected from polypropylene and polyamide-6 packaging.

10. The method of claim 1 where the sterilization temperature is approximately 136° C. and the time is approximately 25 minutes.

11. The method of claim 1 where the impression material is selected from the group consisting of addition-crosslinking silicone impression materials, condensation-crosslinking silicone impression materials, addition, condensation, and aziridine-group crosslinking polyether impression materials, and impression materials with crosslinking acrylate or methacrylate groups.

12. The method of claim 1 where the primary packaging and the accessories are stable under steam sterilization conditions, and the primary packaging and the accessory material do not affect the material properties of the impression material and/or its components.

13. The method of claim 1 where the steam sterilization is performed at a maximum temperature of 138° C., a maximum pressure of 2.3 bar, and for a maximum time of 30 minutes.

14. A method of obtaining an impression of a body part of a patient in the field of medicine or dentistry comprising applying an appropriate amount of a material selected from the group consisting of addition-crosslinking silicone impression materials, condensation-crosslinking silicone impression materials, addition, condensation, and aziridine-group crosslinking polyether impression materials, and impression materials with crosslinking acrylate or methacrylate groups where the material has had microbial contamination eliminated according to the method of claim 1.

15. A method of using impression materials for the transfer of structures used in micro contact printing of a biological or medicinally active substrate comprising selecting an impression material from the group consisting of addition-crosslinking silicone impression materials, condensation-crosslinking silicone impression materials, addition, condensation, and aziridine-group crosslinking polyether impression materials, and impression materials with crosslinking acrylate or methacrylate groups where the material has had microbial contamination eliminated according to the method of claim 1.

* * * * *